(12) United States Patent
Suh

(10) Patent No.: US 12,332,202 B2
(45) Date of Patent: Jun. 17, 2025

(54) METAL PROPERTY MEASUREMENT SYSTEM AND METHOD

(71) Applicant: RAYNAR CO., LTD., Daejeon (KR)

(72) Inventor: Dong Man Suh, Daejeon (KR)

(73) Assignee: RAYNAR CO., LTD., Daejeon (KR)

( * ) Notice: Subject to any disclaimer, the term of this patent is extended or adjusted under 35 U.S.C. 154(b) by 123 days.

(21) Appl. No.: 17/777,334

(22) PCT Filed: Nov. 18, 2020

(86) PCT No.: PCT/KR2020/016246
§ 371 (c)(1),
(2) Date: May 17, 2022

(87) PCT Pub. No.: WO2021/101237
PCT Pub. Date: May 27, 2021

(65) Prior Publication Data
US 2022/0412906 A1    Dec. 29, 2022

(30) Foreign Application Priority Data

Nov. 18, 2019  (KR) .......................... 10-2019-0147336

(51) Int. Cl.
*G01N 27/02* (2006.01)
*G01N 27/82* (2006.01)

(52) U.S. Cl.
CPC ........... *G01N 27/028* (2013.01); *G01N 27/82* (2013.01)

(58) Field of Classification Search
CPC ...... G01N 27/80; G01N 33/20; G01N 27/028; G01N 27/026; G01N 27/82
See application file for complete search history.

(56) References Cited

U.S. PATENT DOCUMENTS

| | | | | |
|---|---|---|---|---|
| 5,453,689 A | * | 9/1995 | Goldfine | ................ G01N 27/72 324/207.17 |
| 2004/0201380 A1 | * | 10/2004 | Zimmermann | .......... G01V 3/06 600/407 |

(Continued)

FOREIGN PATENT DOCUMENTS

| CN | 105784790 A | 7/2016 |
|---|---|---|
| KR | 20020011662 A | 2/2002 |

(Continued)

OTHER PUBLICATIONS

Andrade et al., "Cement Paste Hardening Process Studied by Impedance Spectroscopy", Elsevier Science Ltd., Electrochimica Acta, 1999, pp. 4313-4318, vol. 44, No. 24.

(Continued)

*Primary Examiner* — Eman A Alkafawi
*Assistant Examiner* — Suresh K Rajaputra
(74) *Attorney, Agent, or Firm* — Goldilocks Zone IP Law

(57) ABSTRACT

Provided is a metal property measurement system and method. Impedance tomography can be performed by means of magnetic field signals reflected from a metal by applying various frequencies to the metal component, and crack or heat treatment defect inspection, classification, correction inspection, and the like for the component can be performed by means of magnetic resonance, without having to strike the component, by using a magnetic resonance sensor for measuring impedance by generating magnetic resonance by applying multi-frequency currents.

10 Claims, 14 Drawing Sheets

(56) References Cited

U.S. PATENT DOCUMENTS

| | | | | |
|---|---|---|---|---|
| 2007/0150238 | A1* | 6/2007 | Struempler | G01N 27/90 |
| | | | | 702/189 |
| 2008/0001609 | A1* | 1/2008 | Kojima | G01N 27/9046 |
| | | | | 324/632 |
| 2012/0245873 | A1* | 9/2012 | Donnangelo | G01N 27/02 |
| | | | | 324/201 |
| 2013/0113499 | A1* | 5/2013 | Golt | G01N 27/041 |
| | | | | 324/600 |
| 2014/0084910 | A1* | 3/2014 | Makino | G01N 27/80 |
| | | | | 324/240 |
| 2018/0188209 | A1 | 7/2018 | Makino | |

FOREIGN PATENT DOCUMENTS

| | | |
|---|---|---|
| KR | 1020080001609 A | 1/2008 |
| KR | 1020130019872 A | 2/2013 |
| KR | 1020140033395 A | 3/2014 |
| KR | 1020140063137 A | 5/2014 |
| KR | 1020180018814 A | 2/2018 |

OTHER PUBLICATIONS

Bonora et al., "Electrochemical Impedance Spectroscopy as a Tool for Investigating Underpaint Corrosion", Elsevier Science Ltd., Electrochimica Acta, 1996, pp. 1073-1082, vol. 41, Nos. 7/8.

Savolainen et al., "An Electrical Impedance Tomography Measurement System for Experimental Use", American Institute of Physics, 1996, pp. 3605-3609, vol. 67, No. 10.

Yin et al., "A multi-frequency impedance analysing instrument for eddy current testing", Institute of Physics Publishing, Measuremet Science and Technology, 2006, pp. 292-402, vol. 17.

* cited by examiner $f_{mix} = f_1 + f_2 + f_3 \ldots + f_8$

METAL PROPERTY MEASUREMENT SYSTEM AND METHOD

CROSS-REFERENCE TO RELATED APPLICATIONS

This application is the United States national phase of International Application No. PCT/KR2020/016246 filed Nov. 18, 2020, and claims priority to Korean Patent Application No. 10-2019-0147336 filed Nov. 18, 2019, the disclosures of which are hereby incorporated by reference in their entirety.

BACKGROUND OF THE INVENTION

Field of the Invention

The present invention relates to a metal property measurement system and method, and more particularly, to a metal property measurement system and method in which a metal property can be measured by means of magnetic field signals reflected from a metal by applying various frequencies to the metal component.

Description of Related Art

Accidents frequently occur worldwide due to defects such as cracks, heat treatment, dimensions, specific gravity, roughness, etc. caused by a vehicle component, a secondary battery, a sintered metal component, etc., and thus, recently, inspection technology for defects in a secondary battery and vehicle component has emerged as an important issue. In particular, non-destructive inspection technology for microcracks is required, and large-scale explosion accidents caused by thermal insulation materials occur frequently, resulting in an astronomical loss of 2600 trillion won worldwide every year, and loss of many lives. Accordingly, recently, replacement of aging pipes due to corrosion and thickness measurement of old pipes has emerged as an important issue.

As a non-destructive inspection technology, an eddy current inspection can be proposed, but the eddy current inspection is a method of generating an eddy current in a conductor and measuring a change in impedance, and the biggest difficulty is a penetration depth of a magnetic field. Due to the skin effect, the magnetic field of a coil flows only on a surface of the conductor, and when only a low frequency of a specific frequency is used, it is difficult to detect a defects of a different depth, and there is disadvantage of having to perform an inspection while moving a component or moving a sensor, and thus it is difficult to inspect a complex component.

In addition, the sintered component has the advantages of reducing post-processing costs because the sintered component can be manufactured in a shape close to a final product using a high-precision mold, being widely used in the production of vehicle component because it is possible to reduce assembly costs by integrating two or more components, and thus the effect of cost reduction through mass production is great, and optimizing a material and preventing material wastage because it is possible to use a composite material that is not in a molten alloy due to the combination of materials. However, a filling density of an injection molded body can be non-uniform, and there is a possibility that a defect such as deformation during sintering or cracking or swelling of the molded body during degreasing can occur. However, other than the destructive inspection method, there is no proper method of detecting the occurrence of the defects such as crack, deformation, a specific gravity change, etc. before and after molding.

In order to solve this demand, in the metal property measurement system and method according to an embodiment of the present invention, through reliable comparison data (reference data) for not only a normal product but also an abnormal product (a defective product, etc.) under various conditions, a system performing verification of a thermal curing process through a comparative analysis of measurement data is disclosed.

In this regard, Korean Patent Application Laid-Open No. 10-2002-0011662 ("Method of Measuring Internal Defect of Metal Material Using Laser-Guided Ultrasonic Waves") discloses a method of projecting laser on a metal material to be measured to generate ultrasonic waves inside the metal material, installing a non-contact ultrasonic transducer at a certain distance from a surface opposite to a surface where the metal material collides with the laser, receiving the ultrasonic waves passing through the metal material by the non-contact ultrasonic transducer, analyzing the ultrasonic waves received by the non-contact ultrasonic transducer, and measuring an internal defects of the metal material. However, a method of inspecting a crack defect of a powder sintered product by measuring acoustic resonance by striking through an acoustic resonance method is known, but damage is applied to component by directly striking the component, and the strike after molding can damage the component, and thus there is a limit to an application to defective inspection of sintered component in mass production.

SUMMARY OF THE INVENTION

Technical Problem

An object of the present invention is to provide a metal property measurement system and method that can measure a degree of hardening, a depth, etc. of a heat-treated metal component, by applying various frequencies to a metal component and performing impedance tomography (measurement) by means of a magnetic field signal reflected from a metal.

In addition, an object of the present invention is to provide a metal property measurement system and method that can measure a crack, a degree of hardening, a heat treatment depth, etc. of a metal component by means of magnetic resonance.

Technical Solution

The present invention measures a metal property that measures a degree of hardening, a depth, etc. of a heat-treated metal component, by applying various frequencies to a metal component and performing impedance tomography (measurement) by means of a magnetic field signal reflected from a metal, and measures a metal property that measures a crack, a degree of hardening, a heat treatment depth, etc. of a metal component by means of magnetic resonance.

Advantageous Effects

The metal property measurement system and method of the present invention have an advantage of enabling performance of tomography on a specimen by variously applying low-frequency currents set in advance, in order to overcome the problem that it is difficult to perform an accurate inspection due to a rough surface caused by fusion, etc. in performing a non-destructive inspection on the specimen made of a metal material.

In particular, the metal property measurement system and method of the present invention have an advantage of improving the accuracy of tomography of the specimen by selecting an optimal frequency because various frequencies can be used depending on a metal material component.

In addition, the metal property measurement system and method of the present invention have an advantage of enabling performance of a crack or heat treatment defect inspection for the component, classification and correction inspection for the component, etc. even without striking the component by means of magnetic resonance in performing a non-destructive inspection on a test component made of a metal material.

In addition, the metal property measurement system and method of the present invention have an advantage of easily enabling accurate determination of the problem of a specimen without complicated control, by setting tomography information measured using not only a normal product but also a specimen (an abnormal product, etc.) containing various problems as reference values, classifying measured values using the reference values, and deriving a resultant value.

On the other hand, using the metal property measurement system and method of the present invention, it is possible to classify all kinds of metal products according to a certain standard, to measure a surface hardness of a component that has undergone a heat treatment process, to detect whether rust occurs, to detect a micro-crack inside and outside the component, to detect a micro-crack within a volume, and to detect surface conditions. In addition, it is possible to detect whether welding of a battery or another product is defective, or to inspect and classify cracks in fasteners such as a bolt.

DESCRIPTION OF THE INVENTION

Figure 1:
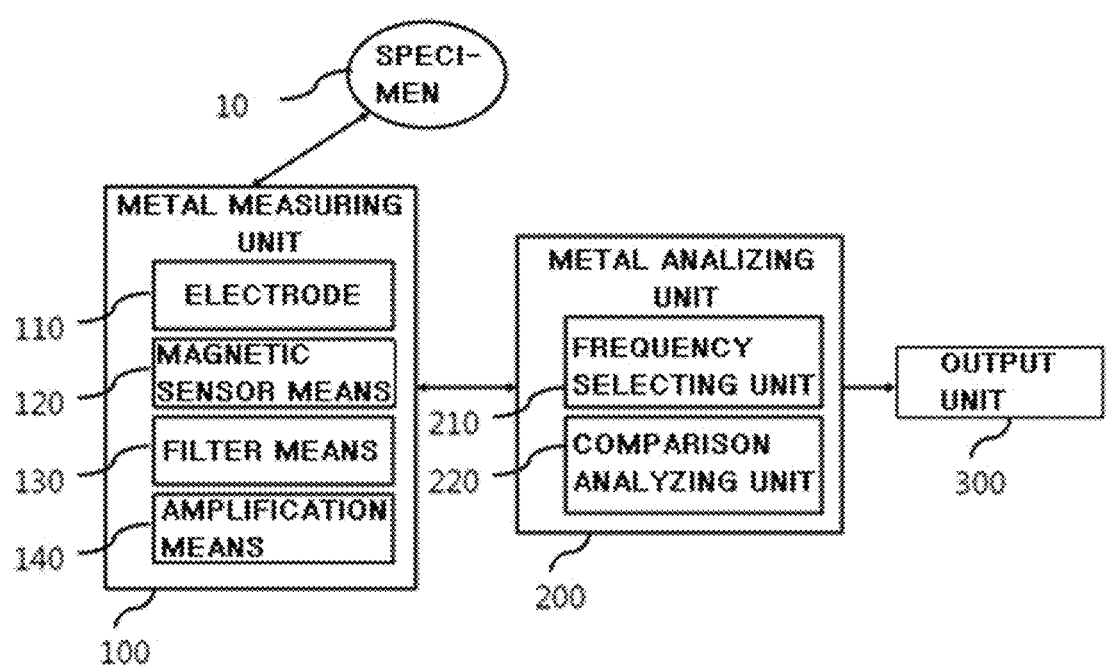
FIG. 1 is an exemplary configuration diagram of a metal property measurement system according to an embodiment of the present invention.

A metal property measurement system according to an embodiment of the present invention is preferably configured to include a metal measuring unit 100 including an electrode 110 measuring impedance by applying a received multi-frequency current to a specimen 10 made of a metal material; and a metal analyzing unit 200 analyzing physical property information of the specimen 10 using the impedance measured by the metal measuring unit 100.

The metal analyzing unit 200 is configured to further include a frequency selecting unit 210 receiving basic information of the specimen 10 according to a preset format and selecting one or more frequencies applied by the metal measuring unit 100, wherein the metal analyzing unit 200 preferably inputs a multi-frequency selected by the frequency selecting unit 210 to the metal measuring unit 100.

The metal analyzing unit 200 is preferably configured to further include a comparison analyzing unit 220 comparing the impedance measured by the metal measuring unit 100 using previously stored reference impedance information, and analyzing the physical property information of the specimen 10.

The metal measuring unit 100 is configured to further include magnetic sensor means 120 measuring a magnetic field flowing through the specimen 10, wherein the metal analyzing unit 200 preferably corrects an error of the impedance using the magnetic field information measured by the magnetic sensor means 120.

The metal measuring unit 100 is preferably configured to further include filter means 130 connected to the magnetic sensor means 120 to remove noise from the intensity of the magnetic field measured by the magnetic sensor means 120; and an amplifying means 140 amplifying the intensity of the magnetic field output from the filter means 130 and transferring the intensity to the metal analyzing unit 200.

The metal property measurement system preferably further includes an output unit 300 configured to include monitoring means and showing physical property information of the specimen 10 analyzed by the metal analyzing unit 200.

A metal property measurement method according to another embodiment of the present invention preferably includes basic information input step (S100) of receiving, in a metal analyzing unit, basic information about a specimen made of a metal material by a preset format; an optimal frequency selection step (S200) of selecting, in the metal analyzing unit, one or more frequencies to be applied to the specimen using the basic information input by the basic information input step (S100); an impedance measuring step (S300) of measuring, in a metal measuring unit, an impedance by applying a multi-frequency current selected by the optimal frequency selection step (S200) to the specimen; and a physical property information analyzing step (S400) of analyzing, in the metal analyzing unit, physical property information of the specimen using the impedance measured in the impedance measuring step (S300).

The metal property measurement method is configured to further include a reference database generating step (S500)

of measuring, in the metal measuring unit, an impedance of a reference specimen of which physical property information is known, and generating, in the metal analyzing unit, reference impedance information.

The physical property information analyzing step (S400) preferably includes analyzing the physical property information of the specimen by comparing the impedance measured in the impedance measuring step (S300), using the reference impedance information generated by the reference database generating step (S500).

A metal property measurement system according to another embodiment of the present invention is preferably configured to include a magnetic resonance sensor 1100 generating magnetic resonance by applying a received multi-frequency current to a test component SP made of a metal material, and measuring an impedance; a signal processor 1200 transmitting a signal for magnetic resonance to the magnetic resonance sensor 1100 and receiving an impedance measurement value; and a signal analyzer 1300 analyzing physical property information of the test component SP using an impedance received through the signal processor 1200.

The magnetic resonance sensor 1100 is configured to include a housing 1110; a magnetic resonance unit 1120 generating magnetic resonance of multiple frequencies; an accommodating unit 1130 forming a space to accommodate the test component SP; and a signal input/output terminal 1140.

The signal analyzer 1300 analyzes the physical property information of the test component SP by comparing the impedance measured by the magnetic resonance sensor 1100 using pre-stored reference impedance information.

The signal analyzer 1300 includes a frequency selecting unit receiving basic information of the test component SP, and the frequency selecting unit receives the basic information of the test component SP and selects one or more frequencies to be applied to the magnetic resonance sensor 1100.

The signal analyzer 1300 is configured to further include an artificial intelligence unit selecting a magnetic resonance frequency, setting at least any one of software amplification, hardware amplification, offset, and gate value, setting and generating a signal suitable for magnetic resonance defect detection, and training a reference value for discriminating good and defective products through an impedance change value analysis.

A metal property measurement method using the metal property measurement system of the present invention includes a step (P100) of selecting N frequencies for multi-frequency mutual interference and magnetic resonance; a step (P200) of setting an allowable value of impedance change for each frequency; a step (P300) of performing a verification inspection on a mock-up sample to inspect good and defective products, or a characteristic of a component; a step (P400) of determining whether the allowable value of impedance change for each frequency presents a reference for determination; a step (P500) of testing a target component through the metal property measurement system; and a step (P600) of determining whether it is a good product/defective product for the target component.

A metal property measurement method using the metal property measurement system of the present invention includes a step (P100) of selecting N frequencies for multi-frequency mutual interference and magnetic resonance; a step (P200) of setting an allowable value of impedance change for each frequency; a step (P300) of performing a verification inspection on a mock-up sample to inspect good and defective products, or a characteristic of a component; an AI training and establishing step (P400') of selecting a magnetic resonance frequency, setting at least one of software amplification, hardware amplification, offset, and gate value, setting and generating a signal suitable for magnetic resonance defect detection, and discriminating good and defective products through an impedance change value analysis; a step (P500) of testing a target component through the metal property measurement system; and a step (P600) of determining whether it is a good product/defective product for the target component.

Hereinafter, a metal property measurement system and method of the present invention will be described in detail with reference to the accompanying drawings. The drawings introduced below are provided as examples in order to sufficiently convey the spirit of the present invention to those skilled in the art. Accordingly, the present invention is not limited to the drawings presented below and can be embodied in other forms. Also, like reference numerals refer to like elements throughout the specification.

At this time, if there is no other definition in the technical terms and scientific terms used, they have the meaning commonly understood by those of ordinary skill in the art to which this invention belongs, and in the following description and accompanying drawings, descriptions of well-known functions and configurations that can unnecessarily obscure the gist of the present invention will be omitted.

In addition, the system refers to a set of components including devices, instruments, means, etc. that are organized and regularly interact to perform necessary functions.

The metal property measurement system and method of the present invention relate to a system and method that can perform tomography on a specimen by variously applying low-frequency currents set in advance, in order to overcome the problem that it is difficult to perform an accurate inspection due to a rough surface caused by a fusion, etc. in performing a non-destructive inspection on the specimen made of a metal material.

In particular, the metal property measurement system and method of the present invention can improve the accuracy of tomography of the specimen through selection of an optimal frequency because various frequencies can be used depending on a metal material component.

In addition, the metal property measurement system and method of the present invention can easily accurately determine the problem of a specimen without control, by setting tomography information measured using not only a normal product but also abnormal products containing various problems as reference values, classifying measured values using the reference values, and deriving a resultant value.

As shown in FIG. 1, the metal property measurement system according to an embodiment of the present invention is preferably configured to include a metal measuring unit 100 and a metal analyzing unit 200.

More specifically to each configuration, the metal measuring unit 100 is preferably configured to include an electrode 110 that applies a current corresponding to multi-frequencies, that is, multiple frequencies, input from the metal analyzing unit 200 to a specimen 10 made of a metal material and measures impedance reflected from the specimen 10. At this time, it is preferable not to simultaneously apply currents corresponding to multiple frequencies to the specimen 10, but to apply a current corresponding to each frequency a plurality of times, that is, it is preferable to receive each of various specific frequencies, apply the corresponding current, and measure the reflected impedance.

The metal analyzing unit 200 preferably analyzes physical property information of the specimen 10 using the impedance of the specimen 10 measured by the metal measuring unit 100, and, in the present invention, can analyze a hardness value (HRC) and a hardness depth (hardness pattern) value by analyzing the impedance and performing the tomography. That is, the metal property measurement system according to an embodiment of the present invention selects a multi-frequency to be applied from the metal measuring unit 100 to the specimen 10 through the metal analyzing unit 200, and applies a magnetic field corresponding to each frequency to the specimen 10 so that impedance tomography can be performed using a magnetic field signal reflected from the specimen 10 by using a depth of penetration of the magnetic field into the specimen 10 different for each frequency, thereby analyzing the impedance tomography and determining the hardness value and the hardness depth value of the specimen 10. Through this, it is possible to determine whether the specimen 10 is defective with very high accuracy.

To this end, as shown in FIG. 1, the metal analyzing unit 200 is preferably configured to include a frequency selecting unit 210 that receives basic information of the specimen 10 according to a preset format. The frequency selecting unit 210 preferably receives the basic information of the specimen 10 and selects one or more frequencies to be applied from the metal measuring unit 100 to the specimen 10. Accordingly, the metal measuring unit 100 preferably applies the multi-frequency (one or more frequencies) selected by the frequency selecting unit 210 to the specimen 10.

In detail, in order to select the multi-frequency (one or more frequencies), the frequency selecting unit 210 approaches a magnetic sensor to the specimen 10 in a non-contact manner in advance, and then measures an impedance value for various frequencies, but selects one or more frequencies at which the impedance value is maximally generated. At this time, by matching and storing the selected one or more frequencies with the measured basic information of the specimen 10, later, when the basic information of the specimen 10 is input to the frequency selecting unit 210, one or more frequencies matching thereto are selected. Here, the frequency selecting unit 210 preferably measures the impedance while changing the frequency from 10 Hz to the maximum frequency to the specimen 10 and applying the frequency to the specimen 10.

Figure 3:
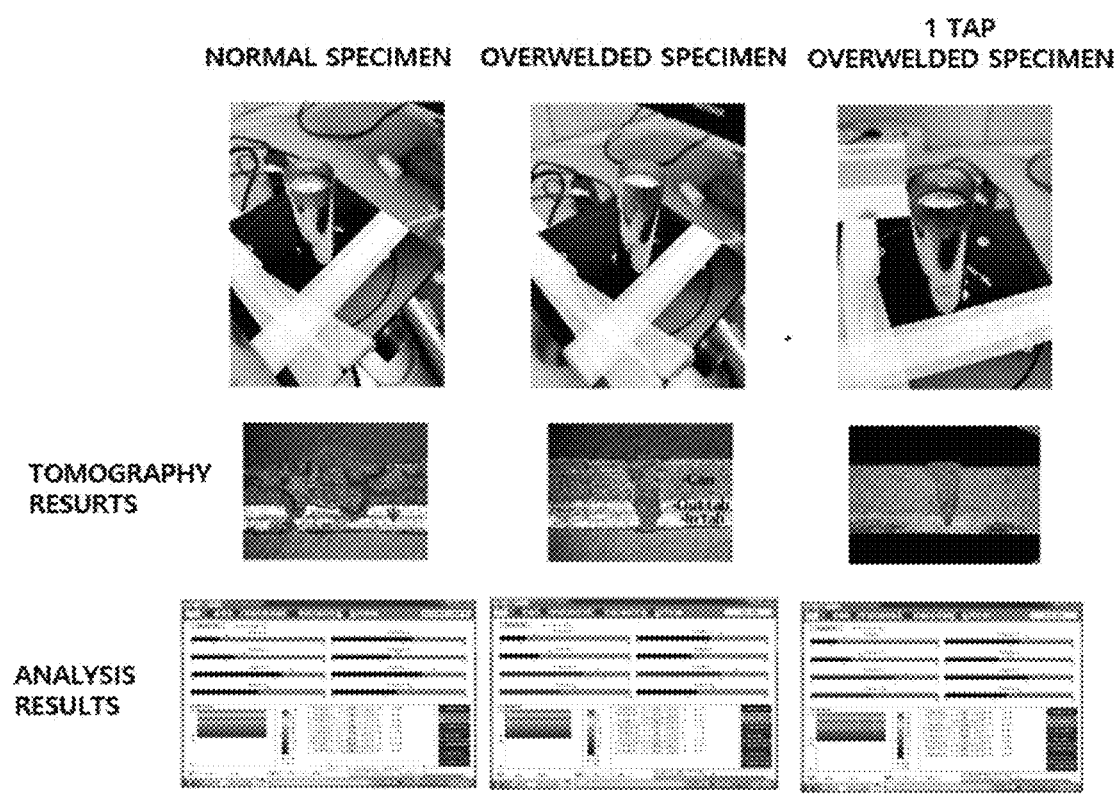
FIGS. 3 and 4 are exemplary diagrams illustrating results obtained by the metal property measurement system according to an embodiment of the present invention.
Figure 4:
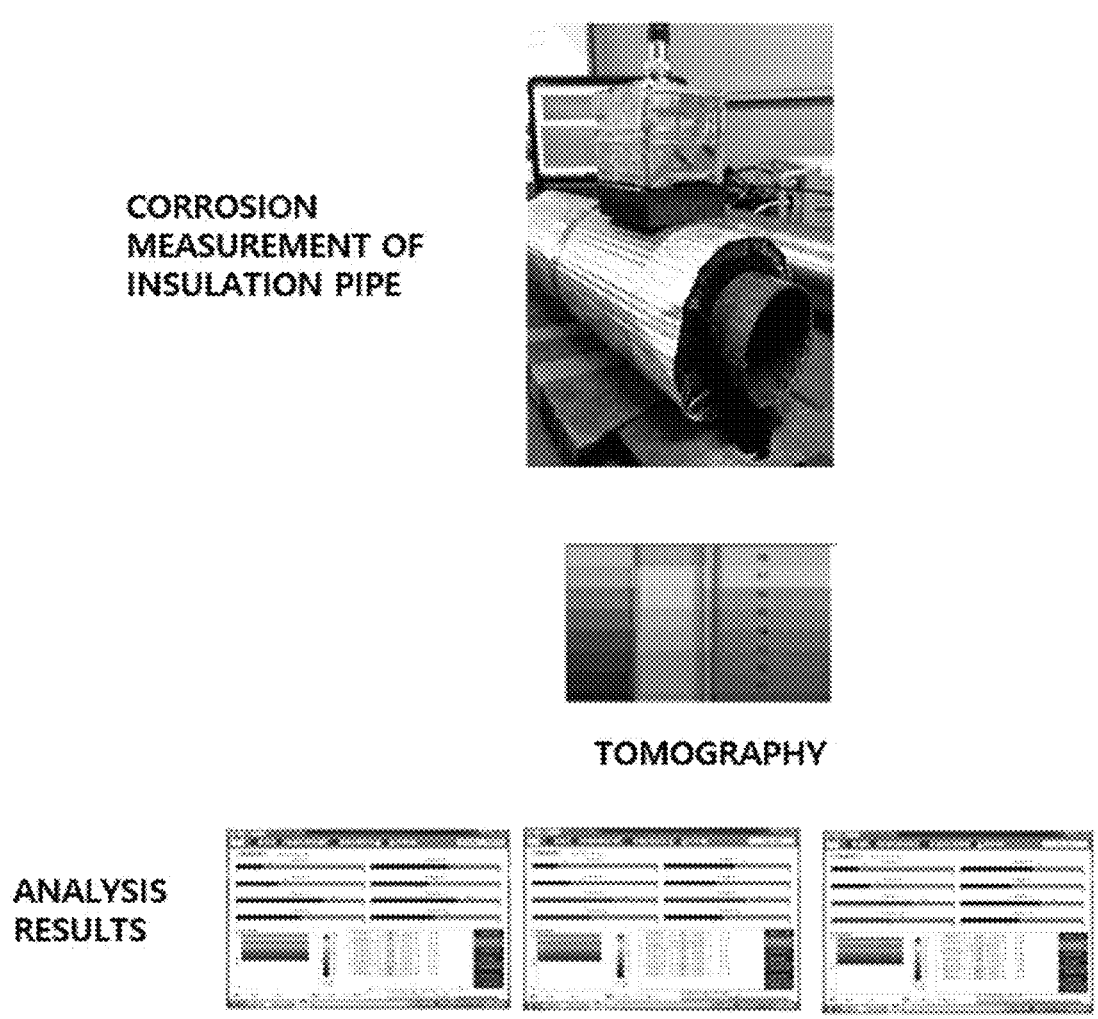

In addition, as shown in FIG. 1, the metal analyzing unit 200 is preferably configured to further include a comparison analyzing unit 220. The comparison analyzing unit 220 can analyze the physical property information of the specimen 10 by comparing the impedance measured by the metal measuring unit 100 using previously stored reference impedance information. In detail, as shown in FIG. 3, the comparison analyzing unit 220 can distinguish a normally welded specimen (left), an overwelded specimen (center), 1 tap overwelded specimen (right), etc., and can also determine to what depth an insulation pipe is corroded as shown in FIG. 4.

At this time, as a reference specimen, it is preferable to generate a reference database for not only a normal product, but also abnormal products that can exist in various ways (defective products, for example, crack occurrence, shape difference, heat treatment state difference, impedance difference, etc.) and store and manage the reference database. Through this, it is possible to determine a group to which the specimen 10 corresponds by comparing the impedance of the specimen 10 measured by the metal measuring unit 100 with the reference database information.

Figure 2:
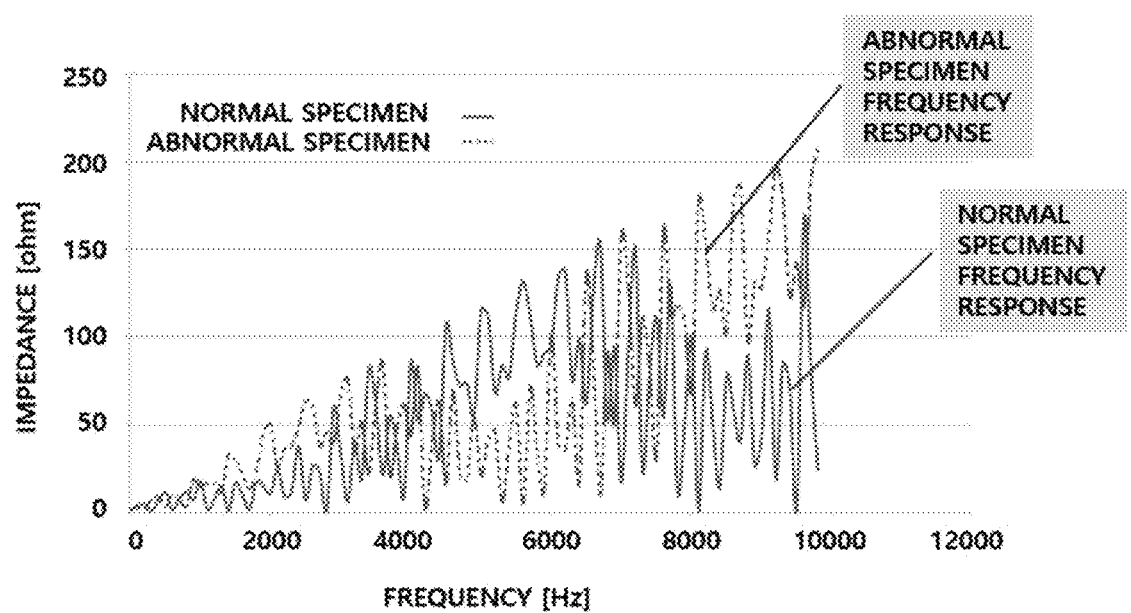
FIG. 2 is an exemplary graph illustrating a frequency response difference between a normal product and an abnormal product, which is used in the metal property measurement system according to an embodiment of the present invention.

In particular, rather than simply determining the group to determine whether it is normal or defective, as described above, it is possible to determine the hardness depth value through tomography results through multiple frequencies, that is, the multi-frequency, and thus, there is an advantage of enabling preparation for a response to a defect more quickly when the defect occurs. In detail, as shown in FIG. 2, the comparison analyzing unit 220 can measure, store, and manage different impedance values according to the respective frequencies for the normal product and the abnormal products, and later determine the group to which the specimen 10 corresponds.

To this end, as described above, the comparison analyzing unit 220 preferably applies each frequency selected to each reference specimen, measures an impedance value, and generates a reference impedance based on the impedance value, in generating reference impedance information through the reference specimen (both normal and abnormal produces).

In addition, as shown in FIG. 1, the metal property measurement system according to an embodiment of the present invention is preferably configured to further include a magnetic sensor means 120 in the metal measuring unit 100. The magnetic sensor means 120 is a configuration that measures a magnetic field flowing through the specimen 10, and more precisely, can measure magnitude of the magnetic field flowing through the specimen 10.

The metal measuring unit 100 can output a current signal corresponding to the intensity of the magnetic field measured by the magnetic sensor means 120, thereby comparing a current of a frequency actually applied through the metal measuring unit 100 and a current applied to the specimen 10 and correcting an error with respect to the impedance measured by the metal measuring unit 100. Through this, the accuracy of the measured value in the metal analyzing unit 200 can be further improved.

As shown in FIG. 1, the metal measuring unit 100 can be configured to further include filter means 130 connected to the magnetic sensor means 120 to remove noise from the intensity of the magnetic field measured by the magnetic sensor means 120. The filter means 130 is preferably configured to include a low pass filter (LPF) or a high pass filter (HPF) for noise removal. In addition, the metal measuring unit 100 is preferably configured to further include an amplifying means 140 that amplifies the intensity of the magnetic field output from the filter means 130 and transfers the intensity to the metal analyzing unit 200.

As such, the metal analyzing unit 200 can compare and analyze the reference impedance information stored in advance using the corrected impedance transmitted from the metal measuring unit 100, determine the group to which the specimen 10 corresponds, and determine even the hardness depth value through the tomography results, and thus there is an advantage of enabling preparation for the response to a defect more quickly when the defect occurs. In detail, the metal analyzing unit 200 compares the impedance value with reference impedance information stored in advance using the corrected impedance received from the metal measuring unit 100, selects a frequency at which a difference occurs, and, at this time, selects at least 8, 16, 32, 64, etc. frequencies.

In addition, as shown in FIG. 1, the metal property measurement system according to an embodiment of the present invention is preferably configured to further include an output unit 300. The output unit 300 is preferably configured to include monitoring means, and preferably show the physical property information of the specimen 10 analyzed by the metal analyzing unit 200, that is, resultant values.

Figure 5:
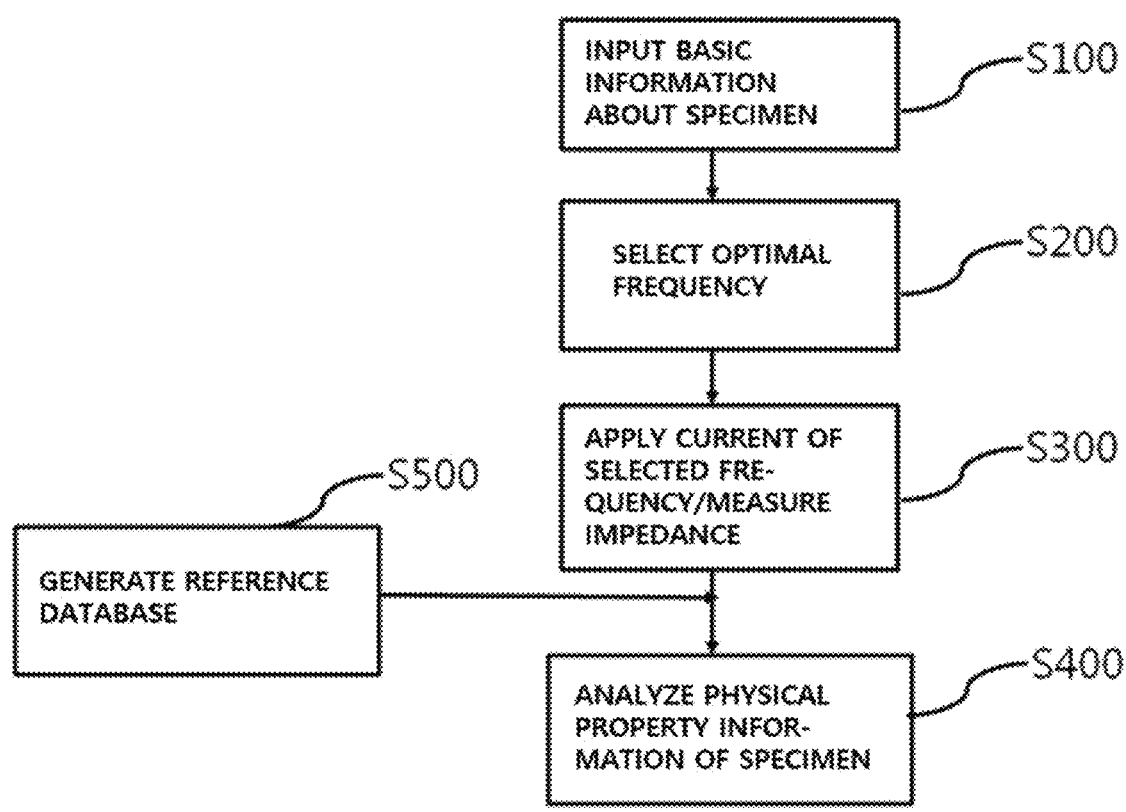
FIG. 5 is a flowchart of a metal property measurement method according to an embodiment of the present invention.

As shown in FIG. 5, the metal property measurement method according to an embodiment of the present invention preferably includes a basic information inputting step (S100), an optimal frequency selecting step (S200), an impedance measuring step (S300), and a material property information analyzing step (S400). More specifically to each step, in the basic information inputting step (S100), basic information about the specimen 10 made of a metal material is received in a preset format by the metal analyzing unit 200.

In the optimal frequency selecting step (S200), the metal analyzing unit 200 selects one or more frequencies to be applied to the specimen 10 using the basic information input by the basic information inputting step (S100). In detail, in the basic information inputting step (S100), the frequency selecting unit 210 of the metal analyzing unit 200 receives the basic information about the specimen 10, and then selects the one or more frequencies to be applied to the specimen 10. To this end, in order to select a multi-frequency (one or more frequencies), the frequency selecting unit 210 approaches a magnetic sensor to the specimen 10 in a non-contact manner in advance, and then measures an impedance value for various frequencies, while selecting the one or more frequencies at which the maximum impedance value occurs. At this time, by matching and storing the selected one or more frequencies with the basic information of the measured specimen 10, later, when the basic information of the specimen 10 is input to the frequency selecting unit 210, the one or more frequencies matching thereto are selected. Here, the frequency selecting unit 210 preferably measures impedance while changing the frequency from 10 Hz to the maximum frequency to the specimen 10 and applying the frequency to the specimen 10.

In the impedance measuring step (S300), the metal measuring unit 100 measures the impedance by applying a current of the multi-frequency selected by the optimal frequency selecting step (S200) to the specimen 10. In detail, the impedance reflected from the specimen 10 is measured by applying a current corresponding to the received multi-frequency, that is, multiple frequencies, through the electrode 110 of the metal measuring unit 100. At this time, it is preferable not to simultaneously apply currents corresponding to the multiple frequencies to the specimen 10, but to apply current corresponding to each frequency a plurality of times, and it is preferable to apply the impedance reflected by applying the corresponding current.

In the physical property information analyzing step S400, the metal analyzing unit 200 analyzes the physical property information of the specimen 10 using the impedance measured in the impedance measuring step S300. At this time, in the metal property measurement method according to an embodiment of the present invention, as shown in FIG. 5, it is preferable to further perform the reference database generating step (S500).

In the reference database generation step (S500), the metal measuring unit 100 measures impedance of a reference specimen of which physical property information is known, and the metal analyzing unit 200 generates reference impedance information, and generates the reference database information. Through this, in the physical property information analyzing step (S400), the impedance measured in the impedance measuring step (S300) is compared by using the reference impedance information generated by the reference database generating step (S500), and the physical property information of the specimen 10 is analyzed.

In detail, in the reference database generating step (S500), the metal measuring unit 100 preferably applies a multi-frequency, measures a reflected impedance, generates a reference database, and generates the reference impedance information with respect to the reference specimen of which hardness value and hardness depth value are already known. At this time, as the reference specimen, it is preferable to generate a reference database of not only a normal product, but also abnormal products that can exist in various ways (defective products, for example, crack occurrence, shape difference, heat treatment state difference, impedance difference, etc.) and store and manage the reference database. Accordingly, in the physical property information analyzing step (S400), a group to which the specimen 10 of the impedance measured in the impedance measuring step (S300) corresponds can be determined using the reference impedance information generated by the reference database generating step (S500).

In particular, rather than simply determining the group to determine whether it is normal or defective, as described above, a hardness depth value can be determined through tomography results through multiple frequencies, that is, the multi-frequency, and thus, there is an advantage of enabling preparation for a response to a defect more quickly when the defect occurs. In detail, as shown in FIG. 2, different impedance values can be measured, stored, and managed according to frequencies for the normal product and the abnormal products, and later the group to which the specimen 10 corresponds can be determined. To this end, as described above, the comparison analyzing unit 220 preferably applies each frequency selected to each reference specimen when generating the reference impedance information through the reference specimen (both normal and abnormal products) while measuring an impedance value, and generating a reference impedance based on the impedance value.

In addition, in the metal property measurement method according to an embodiment of the present invention, in order to further improve the accuracy of the measured value, magnitude of a magnetic field flowing through the specimen 10 is measured and compared with a current of the actually applied frequency, and thus an error with respect to the impedance measured by the metal measuring unit 100 can be corrected. In addition, it is preferable to remove noise from the intensity of the magnetic field measured through the filter means 130, and amplify the intensity of the magnetic field through the amplifying unit 140, and then allow the metal analyzing unit 200 to perform the physical property information analyzing step (S400). According to a request of an outside manager, the metal property measurement method according to an embodiment of the present invention can be configured to further include a monitoring step of outputting a resultant value analyzed in the physical property information analyzing step (S400).

In a metal property measurement system and defect detection method according to another embodiment of the present invention, in performing a non-destructive inspection on a test component SP made of a metal material, crack or heat treatment defect for the component, classification and correction inspection for the component, etc. can be performed without having to strike the component by means of magnetic resonance.

In particular, since various frequencies can be used depending on a metal material component, magnetic resonance of the test component SP can be made by selecting the optimal frequency for this, thereby improving the accuracy of defect detection.

In addition, the metal property measurement system and defect detection method according to another embodiment of the present invention can accurately determine a problem of the test component SP easily without complicated control, by setting tomography information measured using not only a normal product but also abnormal products containing various problems as reference values, classifying measured values using the reference values, and deriving a resultant value.

Figure 6:
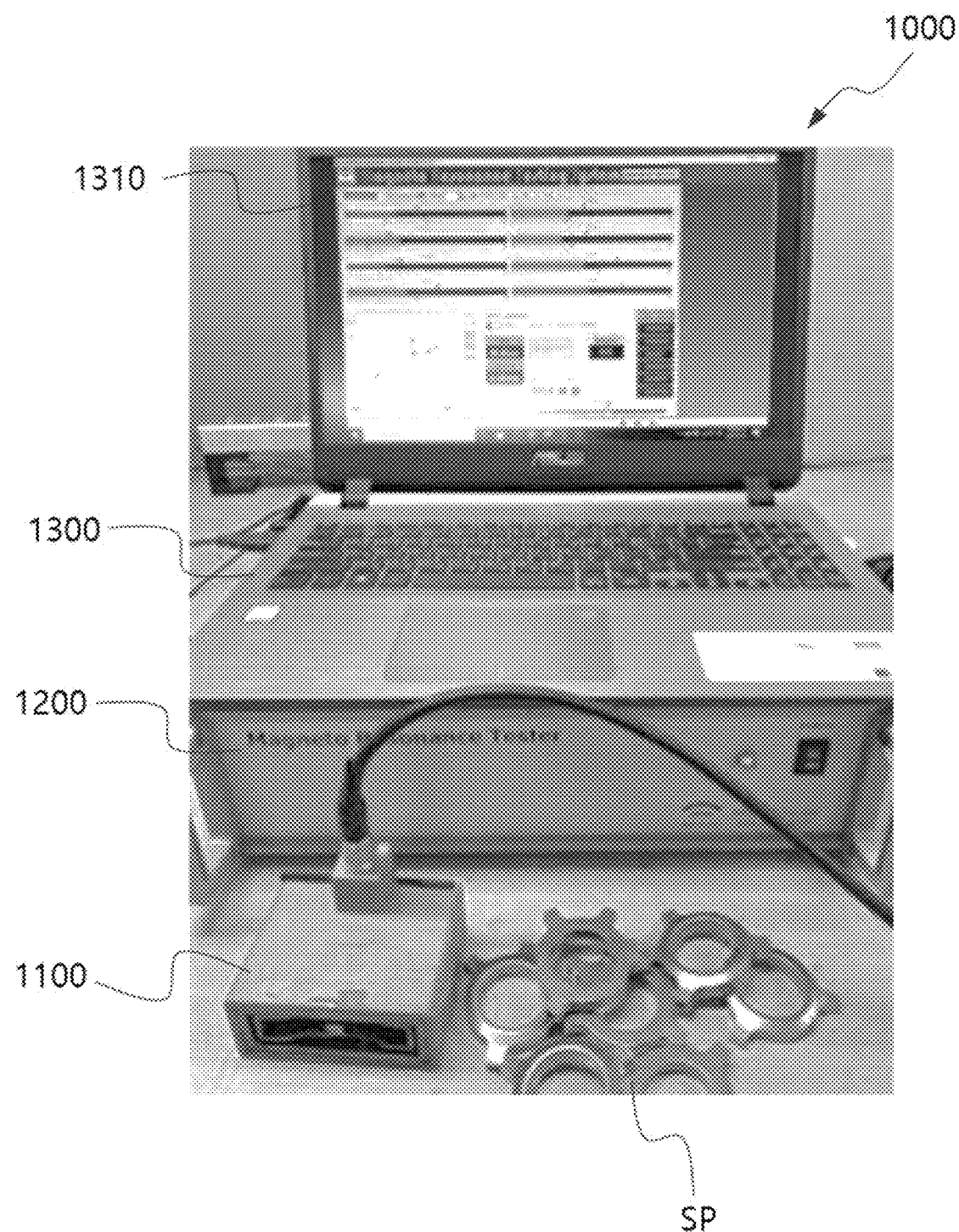
FIG. 6 is an exemplary configuration diagram of a metal property measurement system according to another embodiment of the present invention.

As shown in FIG. 6, the metal property measurement system according to another embodiment of the present invention is preferably configured to include a magnetic resonance sensor, a signal processor, a signal analyzer, and a screen displaying defect detection results.

More specifically to each configuration, the magnetic resonance sensor 1100 applies a current corresponding to a multi-frequency input from the signal processor 1200, that is, multiple frequencies, to the test component SP made of a metal material, causes magnetic resonance in the test component SP, receives an impedance signal at that time, and detects a state of the test component SP.

Figure 7:
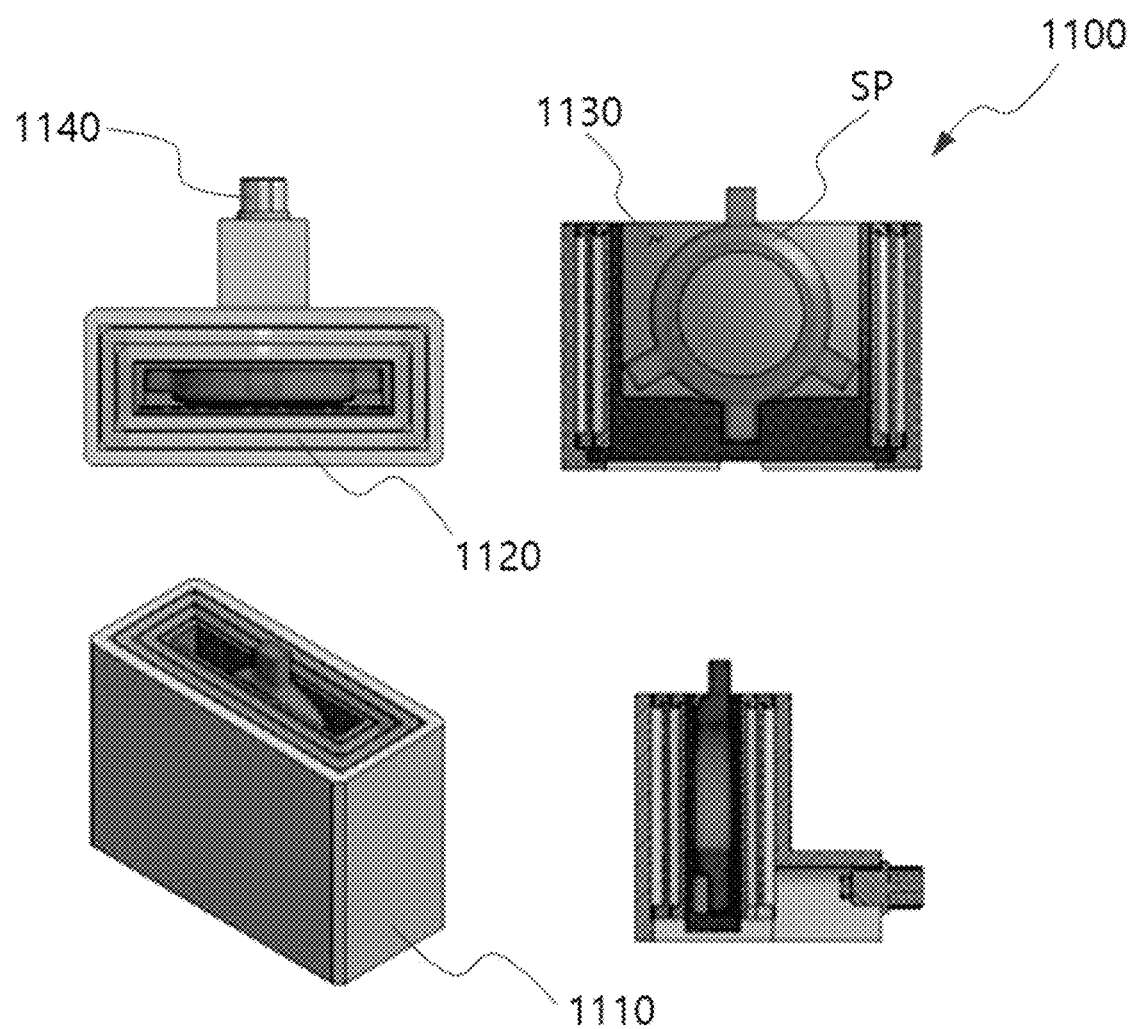
FIG. 7 is an exemplary view of a magnetic resonance sensor of the metal property measurement system according to the present invention.

With respect to a detailed configuration of the magnetic resonance sensor 1100 through FIG. 7, the magnetic resonance sensor 1100 of the present invention is configured to include a housing 1110, a magnetic resonance unit 1120 that generates magnetic resonance of multiple frequencies, an accommodating unit 1130 that forms a space to accommodate the test component SP, and a signal input/output terminal 1140.

That is, when the test component SP is inserted into the accommodating unit 1130 and a signal generating magnetic resonance is input through the signal input/output terminal 1140, the magnetic resonance occurs in the magnetic resonance unit 1120 in the housing 1110, and impedance of a signal generated at this time is analyzed and compared with a reference value, and thus it is determined whether a crack has occurred in the test component SP.

The signal processor 1200 preferably generates a signal to implement the magnetic resonance in the magnetic resonance sensor 1100, is formed to measure the impedance of the test component SP, and analyzes physical property information of the test component SP by using the signal analyzer 1300, and in the present invention, it is determined whether a crack, heat treatment defect, etc. occurs by analyzing the measured impedance of the test component SP.

That is, the metal property measurement system according to an embodiment of the present invention can select a multi-frequency to be applied to the test component SP in the magnetic resonance sensor 1100 through the signal processor 1200, generate magnetic resonance suitable to the test component SP for each frequency by applying a magnetic field corresponding to each frequency to the test component SP, and determine whether the test component SP is defective with very high accuracy by using a magnetic field signal reflected from the test component SP.

To this end, the signal analyzer 1300 is preferably configured to include a frequency selecting unit that receives basic information of the test component SP, and the frequency selecting unit receives the basic information of the test component SP and selects one or more frequencies to be applied to the magnetic resonance sensor 1100. Accordingly, the magnetic resonance sensor 1100 generates magnetic resonance in the test component SP using the multi-frequency (one or more frequencies) selected by the frequency selecting unit.

In detail, in order to select the multi-frequency (one or more frequencies), the frequency selecting unit generates magnetic resonance in the test component SP in advance and then measures impedance values for various frequencies. For example, the frequency selecting unit preferably measures the impedance while changing a frequency from 10 Hz to the maximum frequency in the magnetic resonance sensor 1100 and applying a magnetic field to the test component SP.

Figure 8:
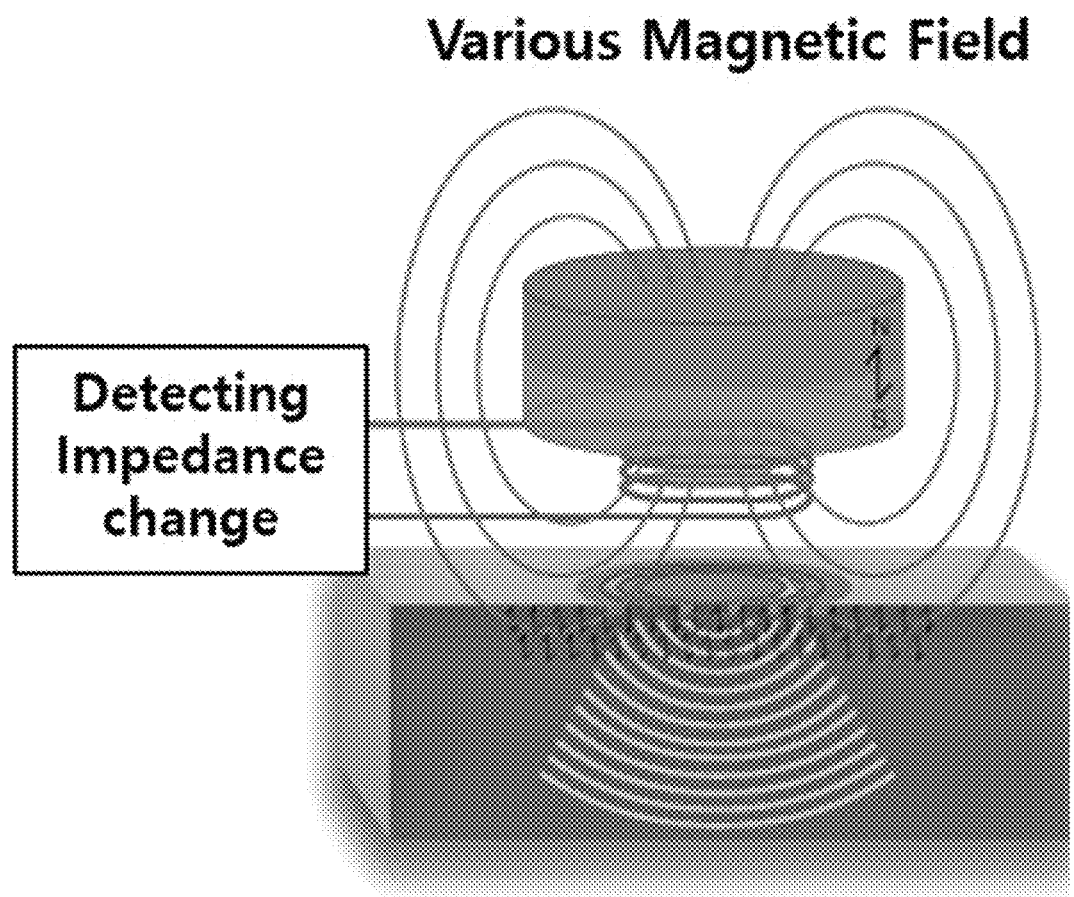
FIG. 8 is a conceptual diagram illustrating a magnetic resonance defect detection principle according to the present invention.

FIG. 8 is a conceptual diagram illustrating a magnetic resonance defect detection principle according to the present invention, and the defect detection principle according to the present invention will be described in more detail with reference to FIG. 8. Magnetic resonance refers to a phenomenon in which a magnetic field resonates with electromagnetic waves, and when an object vibrates according to its natural frequency, a resonance phenomenon in which the amplitude increases, occurs in the magnetic field. In more detail, an atomic nucleus of hydrogen has a state of disordered rotational motion, and when placed in a magnetic field, precession occurs with respect to a direction of the magnetic field. At this time, when electromagnetic waves are irradiated to the atomic nucleus in a precession state, only a frequency resonant with the precession is emitted again, an MRI is an image that is reconstructed by a computer by collecting emitted electromagnetic waves with an antenna, and a clearer image can be obtained by increasing the intensity of the magnetic field.

The method of detecting a defect using magnetic resonance of the present invention is to measure a change in impedance by applying a mutual interference inducing technology by multi-channel frequencies using multiple low-frequency eddy currents, perform a comparison with a reference value, and determine whether the test component is abnormal.

The signal analyzer 1300 of the present invention can analyze the physical property information of the test component SP by comparing the impedance measured by the magnetic resonance sensor 1100 using the reference impedance information stored in advance.

In detail, the signal analyzer 1300 preferably applies the multi-frequency to the normal and defective test component SP, measures the reflected impedance, generates a reference database, and stores and manages the reference database. That is, as the reference test component SP, it is preferable to generate a reference database for not only the normal product, but also abnormal products that can exist in various ways (defective products, for example, crack generation, shape difference, heat treatment state difference, impedance difference, etc.) and store and manage the reference database.

Through this, it is possible to determine a group to which the test component SP corresponds, by comparing the impedance of the test component SP measured by the magnetic resonance sensor 1100 with the reference database information. In particular, rather than simply determining the group to determine whether it is normal or defective, as described above, it is possible to determine an occurrence depth value of crack through tomography results through multiple frequencies, i.e., the multi-frequency, and thus, there is an advantage of enabling preparation for a response to a defect more quickly when the defect occurs.

In detail, the signal analyzer 1300 can measure, store, and manage different impedance values according to respective frequencies for the normal product and the abnormal product and later determine the group to which the test component SP corresponds. To this end, as described above, the signal analyzer 1300 preferably measures an impedance value while applying each frequency selected for each reference test component SP and generates a reference impedance based on the impedance value in generating reference impedance information through the reference test component SP (both the normal and abnormal products).

Figure 9:
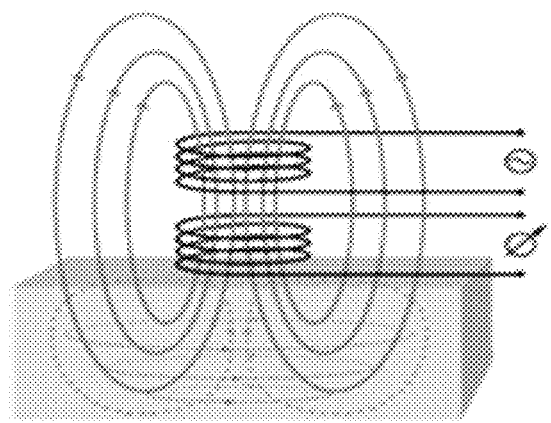
FIG. 9 is a conceptual diagram for explaining mutual interference by multi-channel frequencies according to the present invention.
Figure 9:
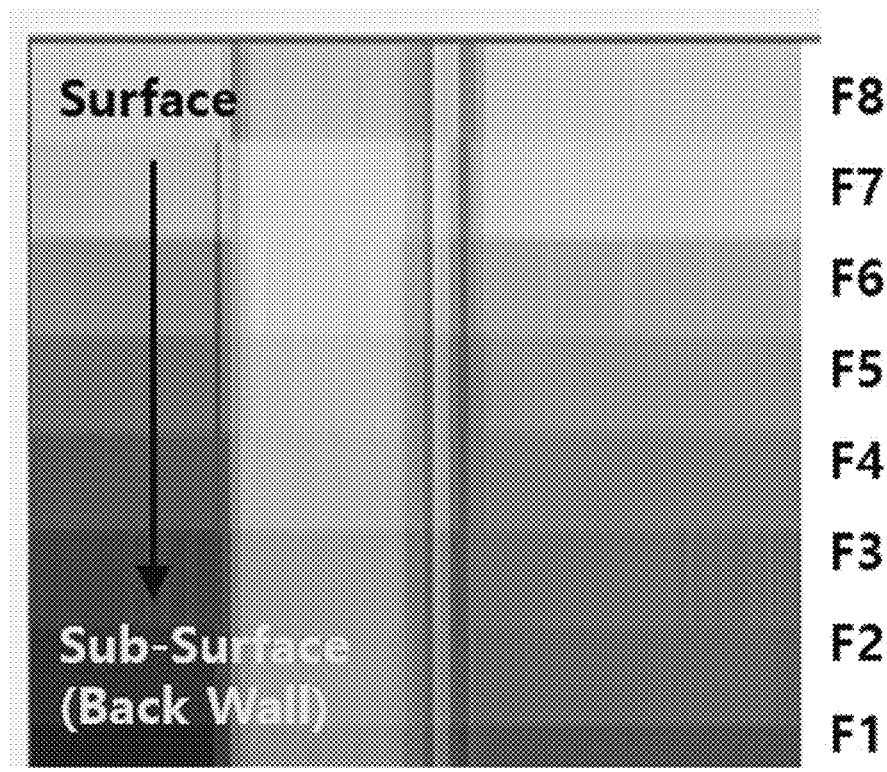

FIG. 9 is a conceptual diagram for explaining a mutual interference inducing technology by a multi-channel frequency. Referring to FIG. 9, for example, when an eddy current is formed using eight frequencies, magnetic resonance can be generated at various depths from the surface of the test component to the inside, and through this, not only the surface of the test component but also even an internal crack can be accurately detected.

Figure 10:
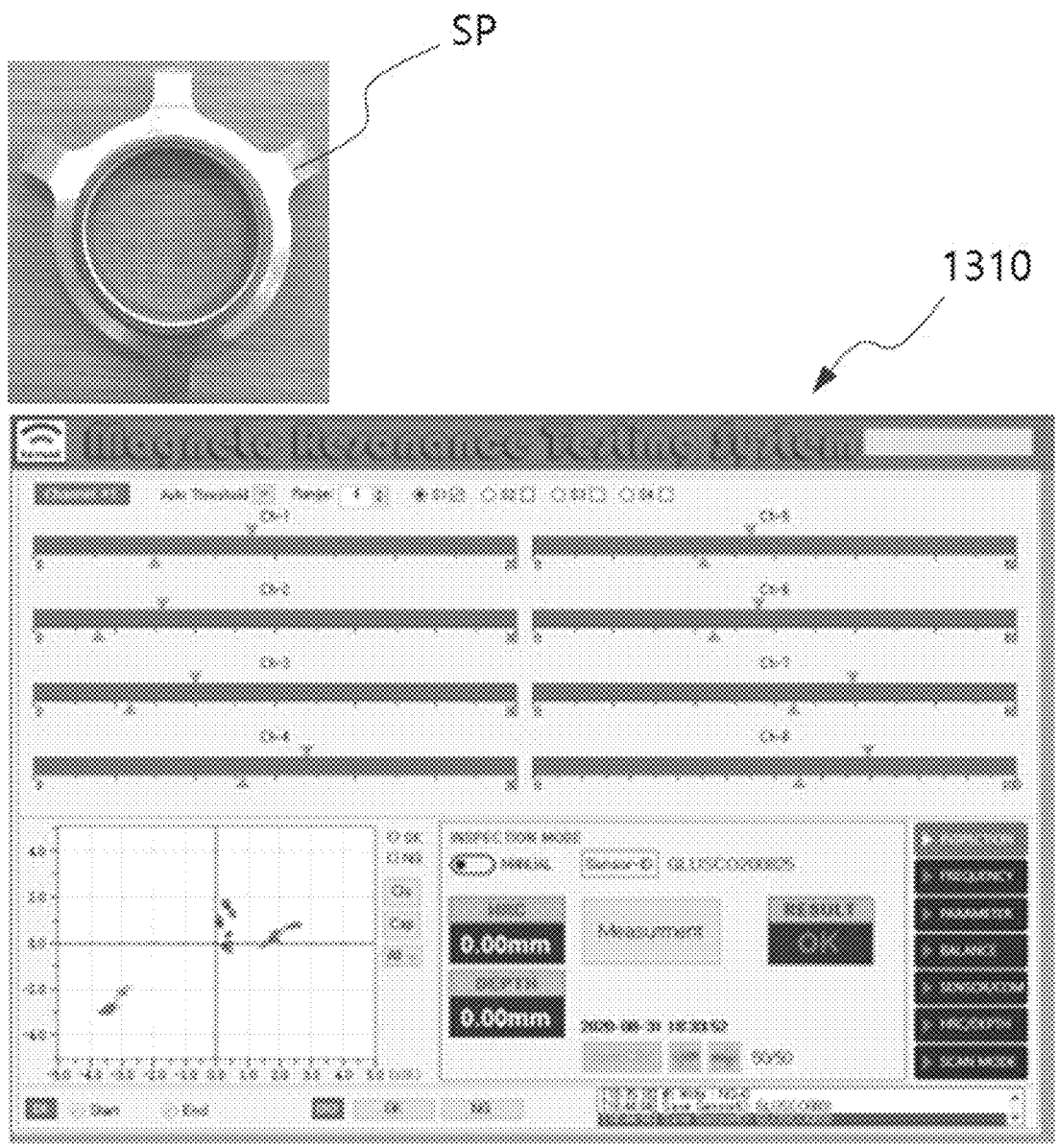
FIGS. 10 and 11 are diagrams illustrating test results of a good product and a defective product according to the metal property measurement system of the present invention.
Figure 11:
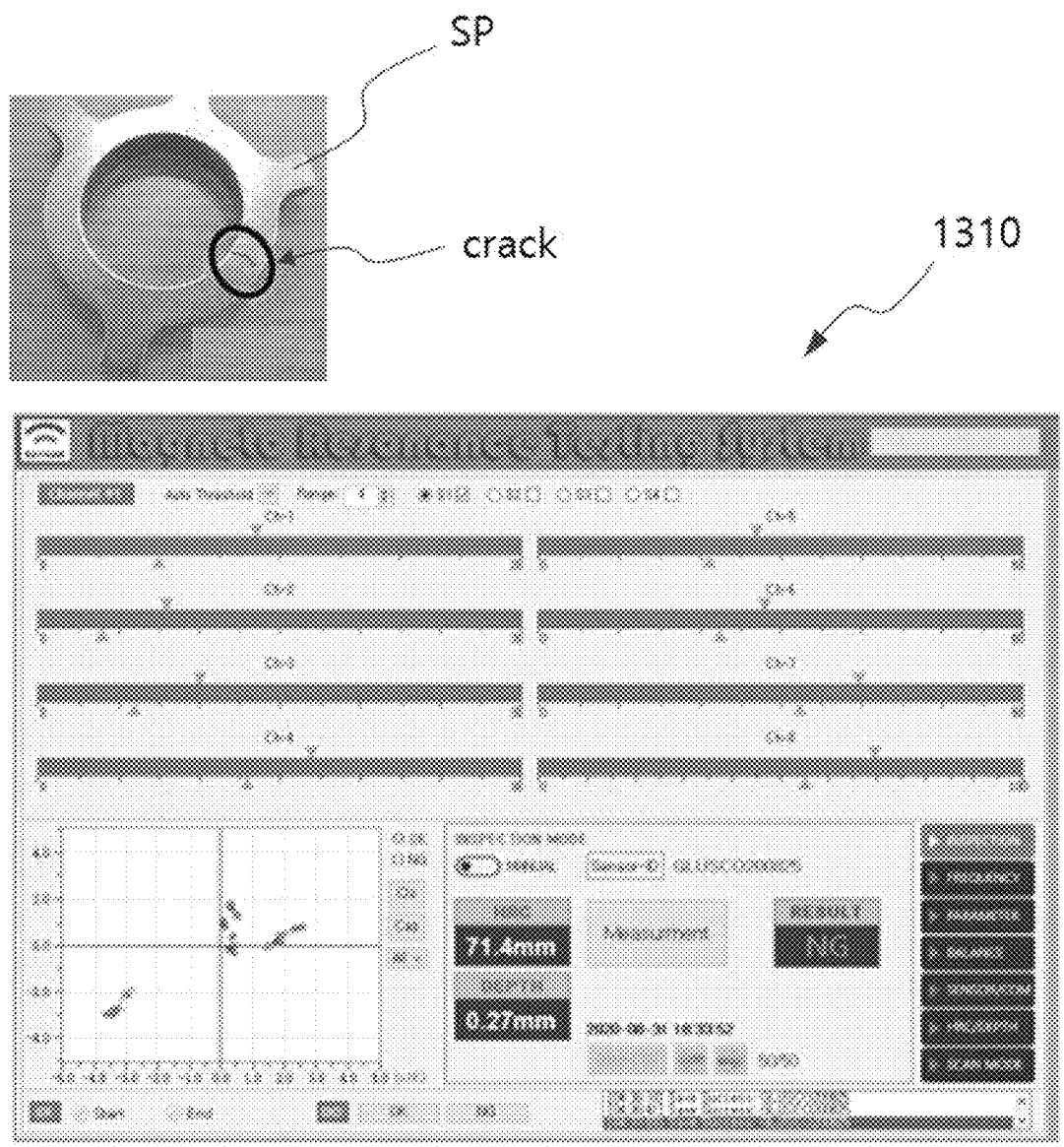

FIGS. 10 and 11 are diagrams illustrating test results of good and defective products according to the metal property measurement system of the present invention. As in FIG. 10, for example, when magnetic resonance is generated using eight frequencies for the test component SP, which is a sintered component, and a change value of each impedance is measured, if the change value of the impedance is located within a normal range, a screen 1310 displays a defect detection result of 'OK'. On the other hand, as shown in FIG. 11, when some cracks are formed in the test component SP, if the change value of the impedance for each frequency is out of a measurement range in a measurement frequency band, it is comprehensively determined and in the case of a defective product, 'NG' is displayed.

Figure 12:
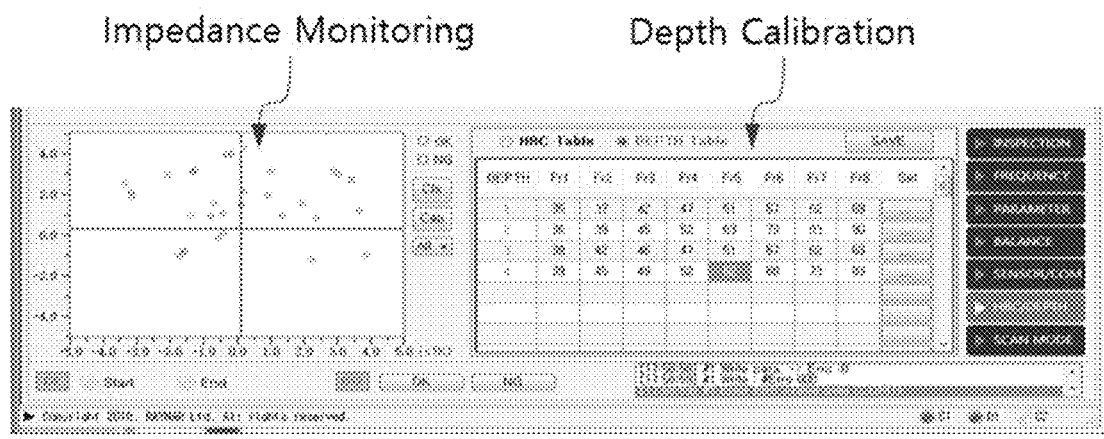
FIG. 12 is a diagram illustrating a screen of the metal property measurement system of the present invention.
Figure 12:
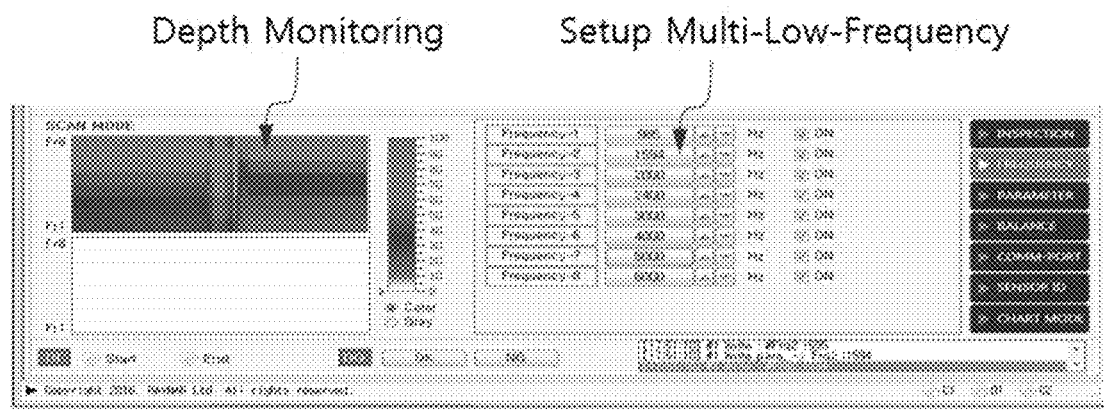

FIG. 12 is a diagram illustrating a screen of a signal analyzer of the metal property measurement system of the present invention. A frequency for generating a multi-frequency signal can be set through the signal analyzer of the present invention, impedance change can be monitored, information according to depth such as heat treatment thickness, etc. can be monitored, or correction of depth can be performed.

Figure 13:
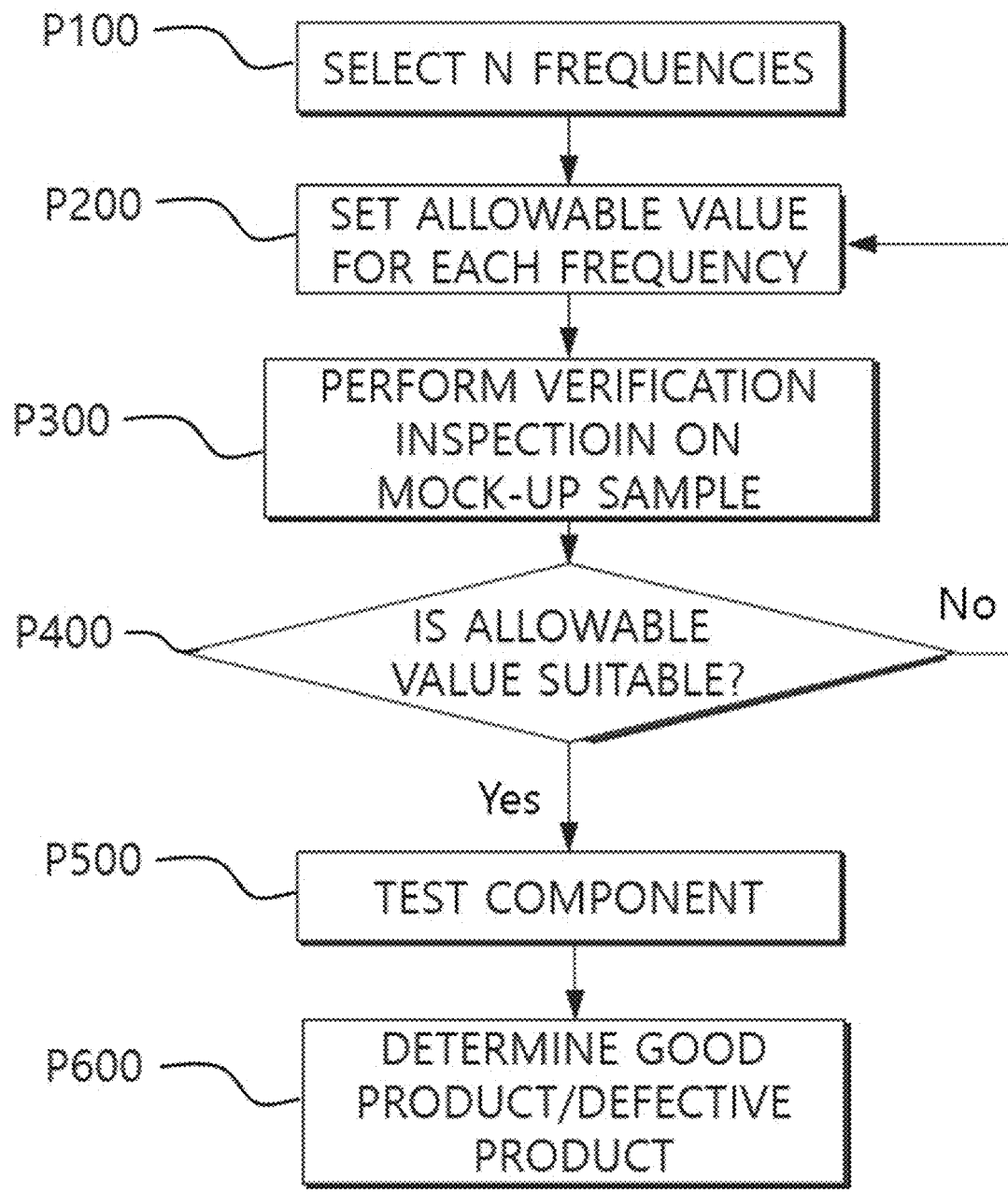
FIG. 13 is a flowchart of the metal property measurement method according to the present invention.

FIG. 13 is a flowchart for explaining the metal property measurement method according to the present invention. Referring to FIG. 13, the metal property measurement method of the present invention is configured to include a step (P100) of selecting N frequencies for multi-frequency mutual interference and magnetic resonance, step (P200) of setting an allowable value of impedance change for each frequency, a step (P300) of performing a verification inspection on a mock-up sample to inspect good and defective products, or various characteristics, a step (P400) of determining whether the allowable value of impedance change for each frequency presents an appropriate reference for determination, a step (P500) of testing a target component through a metal property measurement system, and a step (P600) of determining whether it is a good product/defective product for the target component. At this time, if the allowable value for determining whether the product is good/defective is not appropriate, it returns to a step (P200) of setting the allowable value of impedance change for each frequency to adjust the allowable value.

Figure 14:
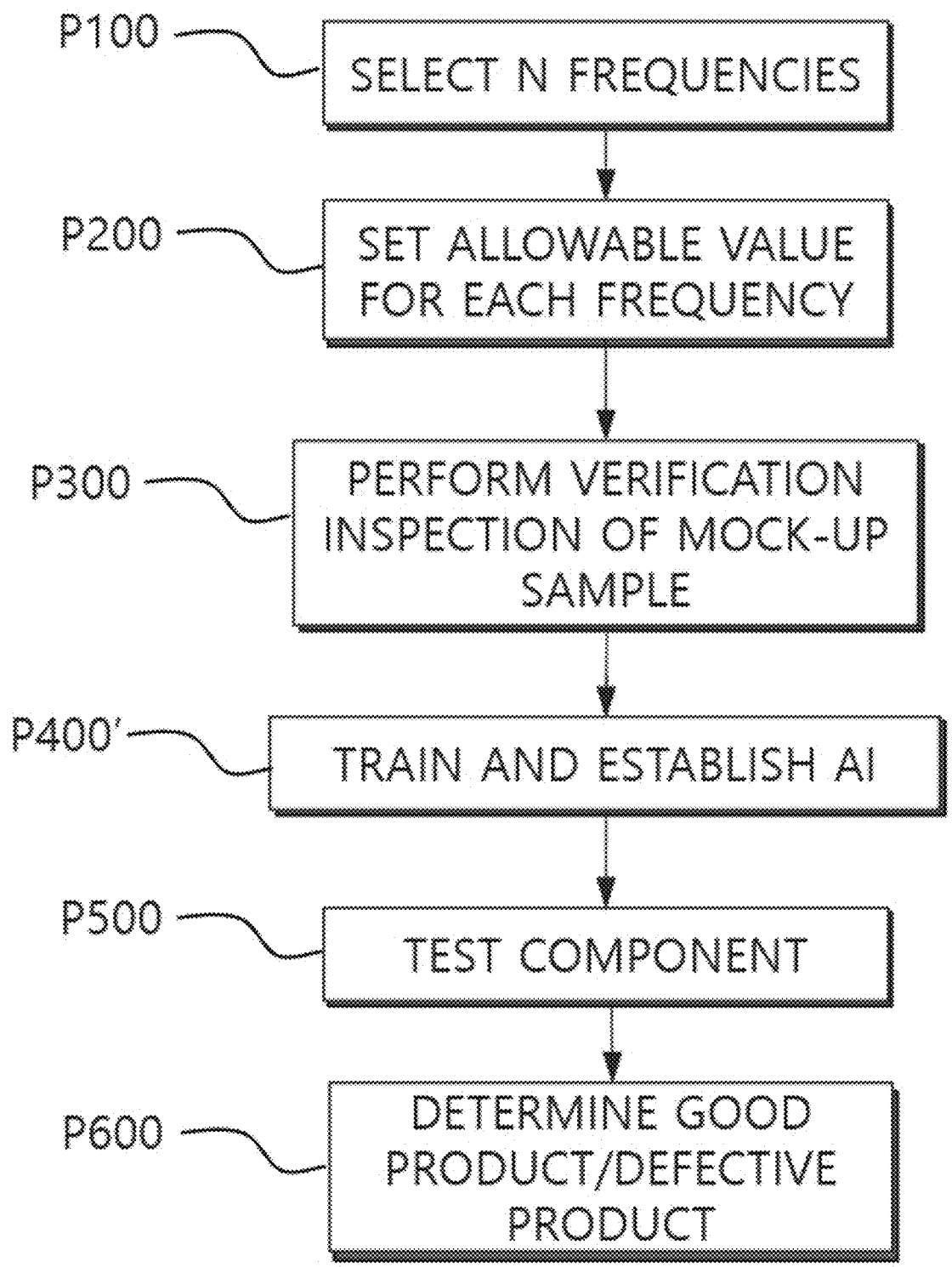
FIG. 14 is a flowchart of a metal property measurement method according to another embodiment of the present invention.

Meanwhile, FIG. 14 is a flowchart for explaining a metal property measurement method according to another embodiment of the present invention, and unlike the defect detection method described above, a defect is determined using an artificial intelligence algorithm. For example, eight to ten magnetic resonance frequencies are selected through a signal processor and signal analyzer, software amplification, hardware amplification, offset, and gate values are set, a signal suitable for magnetic resonance defect detection is set and generated, and, through an impedance change value analysis, a reference value for discriminating good and defective products is trained.

For example, when 2 to 10 pieces of normal component information and 2 to 10 pieces of defective component information are input, and a magnetic resonance frequency, software amplification, hardware amplification, offset, and gate values are changed in various ways to obtain big data about impedance change values, good and defective products for the corresponding component can be determined without separately going through an allowable value adjusting step. That is, through an AI training and establishing step (P400'), a step (P400) of determining whether the allowable value of impedance change for each frequency presents an appropriate reference for determination can be replaced.

On the other hand, using the metal property measurement system and method of the present invention, it is possible to classify all kinds of metal products according to a certain standard, to measure a surface hardness of a component that has undergone a heat treatment process, to detect whether rust occurs, to detect a micro-crack inside and outside the component, to detect a micro-crack within a volume, and to detect surface conditions. In addition, it is possible to detect whether welding of a battery or another product is defective, or to inspect and classify cracks in fasteners such as a bolt.

As described above, in the present invention, specific matters such as specific components and the like and limited embodiment and drawings have been described, but these are only provided to help more general understanding of the present invention, and the present invention is not limited to the above one embodiment, and various corrections and modifications are possible from the description by those of ordinary skill in the art to which the present invention pertains.

Accordingly, the idea of the present invention should not be limited to the described embodiments, and not only the claims to be described later, but also all those with equivalent to the claims or equivalent modifications belong to the scope of the idea of the present invention.

DESCRIPTION OF REFERENCE NUMERALS

10: specimen
100: metal measuring unit
110: electrode 120: magnetic sensor means
130: filter means 140: amplification means
200: metal analyzing unit
210: frequency selecting unit 220: comparison analyzing unit
1000: metal property measurement system
1100: magnetic resonance sensor
1110: housing 1120: magnetic resonance unit
1130: accommodating unit 1140: input/output terminal
1200: signal processor
1300: signal analyzer
1310: screen
SP: Inspection component (SP)

INDUSTRIAL APPLICABILITY

The present invention has industrial applicability since the present invention relates to the metal property measurement.

The invention claimed is:
1. A metal property measurement system comprising:
a metal measuring unit including a magnetic resonance sensor for detecting an electrode measuring impedance by applying a received multi-frequency current for inducing multi-frequency mutual interference to a same position of a specimen made of a metal material; and a metal analyzing unit including a signal processor transmitting a signal for magnetic resonance to the magnetic resonance sensor and receiving an impedance measurement value, analyzing physical property information of the specimen using the impedance measured by the metal measuring unit, wherein the metal analyzing unit includes a frequency selecting unit that receives basic information of the specimen according to a preset format and selects one or more frequencies to be applied by the metal measuring unit, and wherein the metal analyzing unit inputs the multi-frequency, which is a plurality of frequencies selected by the frequency selection unit, to the metal measurement unit, and the electrode applies current corresponding to the input multi-frequency to the same position of the specimen, one frequency at a time, measures the impedance reflected at each frequency, and performs tomography analysis of the specimen based on the analysis of the measured impedance, wherein the metal measuring unit is configured to include magnetic sensor measuring a magnetic field flowing through the specimen in response to the multi-frequency current applied to the same position of the specimen using the multi-frequency mutual interference, and wherein the metal analyzing unit corrects an error of the impedance using the magnetic field information measured by the magnetic sensor.

2. The metal property measurement system of claim 1, wherein the metal analyzing unit is configured to further include a comparison analyzing unit comparing the impedance measured by the metal measuring unit using previously stored reference impedance information, and analyzing the physical property information of the specimen.

3. The metal property measurement system of claim 1, wherein the metal measuring unit is configured to further include filter connected to the magnetic sensor to remove noise from intensity of the magnetic field measured by the magnetic sensor; and an amplifier amplifying the intensity of the magnetic field output from the filter and transferring the intensity to the metal analyzing unit.

4. The metal property measurement system of claim 3, further including an output unit configured to include monitor and show physical property information of the specimen analyzed by the metal analyzing unit.

5. The metal property measurement system of claim 1, wherein the magnetic resonance sensor is configured to include and a housing;

a magnetic resonance unit generating magnetic resonance of multiple frequencies;

an accommodating unit forming a space to accommodate the test component SP; and a signal input/output terminal.

6. The metal property measurement system of claim 1, wherein the signal analyzer analyzes the physical property information of the test component SP by comparing the impedance measured by the magnetic resonance sensor using pre-stored reference impedance information.

7. The metal property measurement system of claim 6, wherein the signal analyzer includes a frequency selecting unit receiving basic information of the test component SP, and wherein the frequency selecting unit receives the basic information of the test component SP and selects one or more frequencies to be applied to the magnetic resonance sensor.

8. The metal property measurement system of claim 7, wherein the signal analyzer is configured to further include an artificial intelligence unit selecting a magnetic resonance frequency, setting at least any one of software amplification, hardware amplification, offset, and a gate value, setting and generating a signal suitable for magnetic resonance defect detection, and training a reference value for discriminating good and defective products through an impedance change value analysis.

9. A metal property measurement method using the metal property measurement system according to claim 1, the metal property measurement method comprising the steps of:

selecting N frequencies for multi-frequency mutual interference and magnetic resonance;

setting an allowable value of impedance change for each frequency of the N frequencies;

performing a verification inspection on a mock-up sample to inspect good and defective products, or a characteristic of a component;

determining whether the allowable value of impedance change for each frequency of the N frequencies presents a reference for determination;

testing a target component through the metal property measurement system; and determining whether it is a good product/defective product based on the analyzed physical property information by performing a tomography analysis on the target component.

10. A metal property measurement method using the metal property measurement system according to claim 8, the metal property measurement method comprising the steps of:

selecting N frequencies for multi-frequency mutual interference and magnetic resonance;

setting an allowable value of impedance change for each frequency of the N frequencies;

performing a verification inspection on a mock-up sample to inspect good and defective products, or a characteristic of a component;

an AI training and establishing step of selecting a magnetic resonance frequency, setting at least any one of software amplification, hardware amplification, offset, and gate value, setting and generating a signal suitable for magnetic resonance defect detection, and discriminating good and defective products through an impedance change value analysis;

testing a target component through the metal property measurement system; and determining whether it is a good product/defective product based on the analyzed physical property information by performing a tomography analysis on the target component.

* * * * *